(12) United States Patent
Xiao et al.

(10) Patent No.: US 11,610,753 B2
(45) Date of Patent: Mar. 21, 2023

(54) SYSTEMS AND METHODS FOR CORRECTION OF POSITION OF FOCAL POINT

(71) Applicant: SHANGHAI UNITED IMAGING HEALTHCARE CO., LTD., Shanghai (CN)

(72) Inventors: Xin Xiao, Shanghai (CN); Tao He, Shanghai (CN); Xi Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/870,904

(22) Filed: May 9, 2020

(65) Prior Publication Data
US 2021/0110989 A1  Apr. 15, 2021

(30) Foreign Application Priority Data

Oct. 11, 2019 (CN) .......................... 201910964318.4

(51) Int. Cl.
*A61B 6/00* (2006.01)
*A61B 6/03* (2006.01)
(Continued)

(52) U.S. Cl.
CPC ............ *H01J 35/153* (2019.05); *A61B 6/032* (2013.01); *A61B 6/08* (2013.01); *A61B 6/40* (2013.01);
(Continued)

(58) Field of Classification Search
CPC ......... A61B 6/032; A61B 6/40; A61B 6/4021; A61B 6/52; A61B 6/5205; A61B 6/54;
(Continued)

(56) References Cited

U.S. PATENT DOCUMENTS

| 4,675,891 A | * | 6/1987 | Plessis | .................. | H01J 35/103 |
| | | | | | 378/125 |
| 4,675,892 A | * | 6/1987 | Plessis | .................... | H01J 35/24 |
| | | | | | 378/126 |

(Continued)

FOREIGN PATENT DOCUMENTS

| CN | 109685877 A | 4/2019 |
| JP | 2006218327 A | 8/2006 |

(Continued)

OTHER PUBLICATIONS

Rolf Behling, Chapter 6: Diagnostic X-Ray Sources from the Inside, Modern Diagnostic X-Ray Sources, Taylor & Francis Group, 177-308, 2016.

(Continued)

*Primary Examiner* — Allen C. Ho
(74) *Attorney, Agent, or Firm* — Metis IP LLC

(57) ABSTRACT

Systems and methods for determining an offset of a position of a focal point of an X-ray tube is provided. The methods may include obtaining at least one parameter associated with an X-ray tube during a scan of a subject. The methods may further include determining a target offset of a position of a focal point based on the at least one parameter and a target relationship between a plurality of reference parameters associated with the X-ray tube and a plurality of reference offsets of reference positions of the focal point. The methods may further include causing, based on the target offset, a correction on the position of the focal point of the X-ray tube.

20 Claims, 8 Drawing Sheets

(51) Int. Cl.

| | |
|---|---|
| *A61B 6/08* | (2006.01) |
| *H01J 35/02* | (2006.01) |
| *H01J 35/06* | (2006.01) |
| *H01J 35/08* | (2006.01) |
| *H01J 35/10* | (2006.01) |
| *H01J 35/14* | (2006.01) |
| *H01J 35/24* | (2006.01) |
| *H01J 35/26* | (2006.01) |
| *H01J 35/30* | (2006.01) |
| *G06T 11/00* | (2006.01) |
| *G21K 1/087* | (2006.01) |
| *G21K 1/093* | (2006.01) |

(52) U.S. Cl.
CPC .............. *A61B 6/4021* (2013.01); *A61B 6/52* (2013.01); *A61B 6/5205* (2013.01); *A61B 6/54* (2013.01); *A61B 6/542* (2013.01); *A61B 6/545* (2013.01); *A61B 6/56* (2013.01); *A61B 6/563* (2013.01); *A61B 6/566* (2013.01); *A61B 6/58* (2013.01); *A61B 6/582* (2013.01); *G06T 11/005* (2013.01); *G21K 1/087* (2013.01); *G21K 1/093* (2013.01); *H01J 35/02* (2013.01); *H01J 35/06* (2013.01); *H01J 35/08* (2013.01); *H01J 35/10* (2013.01); *H01J 35/14* (2013.01); *H01J 35/147* (2019.05); *H01J 35/24* (2013.01); *H01J 35/26* (2013.01); *H01J 35/30* (2013.01); *H01J 35/305* (2013.01)

(58) Field of Classification Search
CPC ........... A61B 6/542; A61B 6/545; A61B 6/56; A61B 6/563; A61B 6/566; A61B 6/58; A61B 6/582; H01J 35/02; H01J 35/06; H01J 35/08; H01J 35/10; H01J 35/14; H01J 35/147; H01J 35/153; H01J 35/24; H01J 35/26; H01J 35/30; H01J 35/305
USPC ............... 378/125, 127, 137, 138, 144, 98.6
See application file for complete search history.

(56) References Cited

U.S. PATENT DOCUMENTS

| | | | | |
|---|---|---|---|---|
| 4,827,494 A * | 5/1989 | Koenigsberg | ............ | H05G 1/52 378/138 |
| 4,991,189 A * | 2/1991 | Boomgaarden | .......... | G21K 1/02 378/19 |
| 5,065,420 A * | 11/1991 | Levene | ................ | H01J 35/153 378/137 |
| 5,550,886 A * | 8/1996 | Dobbs | .................... | A61B 6/032 378/19 |
| 5,566,220 A * | 10/1996 | Saito | ........................ | H05G 1/26 378/138 |
| 6,094,469 A * | 7/2000 | Dobbs | .................... | A61B 6/4021 378/19 |
| 6,252,935 B1 * | 6/2001 | Styrnol | .................... | H01J 35/10 378/137 |
| 6,968,039 B2 * | 11/2005 | Lemaitre | ............... | H01J 35/153 378/138 |
| 6,980,623 B2 * | 12/2005 | Dunham | .................. | A61B 6/06 378/19 |
| 7,001,071 B2 * | 2/2006 | Deuringer | ............ | H01J 35/153 378/205 |
| 7,082,188 B2 * | 7/2006 | Deuringer | ................ | H05G 1/52 378/113 |
| 7,266,179 B2 * | 9/2007 | Deuringer | ................ | H05G 1/52 378/137 |
| 7,286,644 B2 * | 10/2007 | Andrews | .................. | H05G 1/52 378/138 |
| 7,599,472 B2 * | 10/2009 | Bernhardt | .............. | A61B 6/586 378/137 |
| 7,634,045 B2 * | 12/2009 | Popescu | .................. | G21K 1/10 378/10 |
| 7,852,979 B2 * | 12/2010 | Edie | ....................... | A61B 6/405 378/16 |
| 7,869,571 B2 * | 1/2011 | Hsieh | .................... | A61B 6/4028 378/124 |
| 7,945,024 B2 * | 5/2011 | Lemaitre | .................. | H05G 1/52 378/137 |
| 8,457,282 B2 * | 6/2013 | Baorui | .................... | A61B 6/032 378/22 |
| 8,483,361 B2 * | 7/2013 | Sainath | ................ | A61B 6/4233 378/137 |
| 8,488,742 B2 * | 7/2013 | Tsujii | ..................... | A61B 6/405 378/138 |
| 8,724,773 B2 * | 5/2014 | Baruth | ................. | A61B 6/5258 378/52 |
| 8,761,342 B2 * | 6/2014 | Behling | .................... | H05G 1/30 378/207 |
| 8,891,727 B2 * | 11/2014 | Kurochi | ................ | A61B 6/4208 378/19 |
| 8,923,484 B2 * | 12/2014 | Zou | .......................... | H01J 35/28 378/126 |
| 9,538,979 B2 * | 1/2017 | Behling | ................ | A61B 6/4266 |
| 9,549,712 B2 * | 1/2017 | Li | .......................... | A61B 6/586 |
| 9,833,202 B2 * | 12/2017 | Daerr | ................... | A61B 6/4241 |
| 10,019,795 B2 * | 7/2018 | Rudin | ....................... | G06T 7/60 |
| 10,357,222 B2 * | 7/2019 | Hirayu | .................. | A61B 6/5205 |
| 10,383,203 B2 * | 8/2019 | Meiler | .................... | A61B 6/583 |
| 10,455,678 B2 * | 10/2019 | Zhang | ...................... | H05G 1/52 |
| 10,462,888 B2 * | 10/2019 | Guo | ........................ | A61B 6/547 |
| 10,485,492 B2 * | 11/2019 | Koehler | ............... | G02B 5/1866 |
| 10,553,389 B2 * | 2/2020 | Holch | ................... | H01J 35/153 |
| 10,660,601 B2 * | 5/2020 | He | ........................ | A61B 6/4021 |
| 10,667,768 B2 * | 6/2020 | Jiang | .................... | A61B 6/4291 |
| 10,679,817 B2 * | 6/2020 | Du | ......................... | H01J 35/066 |
| 10,750,603 B2 * | 8/2020 | Guo | ........................ | H05G 1/26 |
| 10,893,839 B2 * | 1/2021 | Fan | ....................... | A61B 6/032 |
| 10,898,159 B2 * | 1/2021 | Edic | ..................... | A61B 6/582 |
| 11,039,809 B2 * | 6/2021 | Lemaitre | ............... | H01J 35/153 |
| 11,064,600 B2 * | 7/2021 | Dokania | ................. | A61B 6/40 |
| 11,109,473 B2 * | 8/2021 | Steadman Booker | ...................... | H01J 35/153 |
| 11,116,469 B2 * | 9/2021 | Bartl | ...................... | A61B 6/022 |
| 11,331,055 B2 * | 5/2022 | Erler | ...................... | G01N 23/046 |
| 2005/0029957 A1 | 2/2005 | Lemaitre et al. | | |
| 2011/0274245 A1 | 11/2011 | Baruth et al. | | |
| 2015/0117618 A1 | 4/2015 | Li et al. | | |
| 2018/0358198 A1 | 12/2018 | Du et al. | | |

FOREIGN PATENT DOCUMENTS

| | | |
|---|---|---|
| JP | 2019107203 A | 7/2019 |
| KR | 20190064025 A | 6/2019 |

OTHER PUBLICATIONS

The Extended European Search Report in European Application No. 20199225.2 dated Feb. 23, 2021, 9 pages.

* cited by examiner

600

| Obtaining at least one real-time parameter of the X-ray tube during the scanning process | ∿ 602 |

↓

| Determining the target offset of the focal point according to the target relationship between the at least one parameter of the X-ray tube and the offset of the focal point of the X-ray tube | ∿ 604 |

↓

| Causing a correction on the position of the focal point to be performed according to the target offset of the focal point | ∿ 606 |

Obtaining a first relationship between the thermal capacity of the X-ray tube and the offset of the focal point of the X-ray tube — 702

Obtaining reference offsets of the X-ray tube according to different reference power and reference scanning durations to establish a second relationship among the power of the X-ray tube, the scanning duration, and the offset of the focal point of the X-ray tube — 704

Determining a target relationship between the at least one parameter of the X-ray tube and the offset of the focal point may be determined based on the first relationship and the second relationship — 706

FIG. 7

SYSTEMS AND METHODS FOR CORRECTION OF POSITION OF FOCAL POINT

CROSS-REFERENCE TO RELATED APPLICATIONS

This application claims priority to Chinese Application No. 201910964318.4 filed on Oct. 11, 2019, the entire contents of which are hereby incorporated by reference.

TECHNICAL FIELD

The present disclosure generally relates to imaging devices, and more particularly, relates to systems and methods for determining an offset of the position of the focal point of an X-ray tube, which may be used to perform a correction on the position of the focal point.

BACKGROUND

Imaging technology, such as computed tomography (CT) technology, has been widely used for clinical examination and medical diagnosis. In a CT device, the radioactive scanning source is an X-ray tube. In the X-ray tube, electrons emitted from the filament are accelerated and reach the focal position on the anode target disc. More than 99% of the energy is converted into heat and absorbed by the anode target disc, and only a slight portion of the energy is converted into X-rays. As shown in FIG. 1, the anode target plate of the ball tube is connected to the anode seat by a ball and a bearing shaft. Heat is transferred from the target disc to the bearing shaft while the X-ray tube is working. Since the temperature of each part of the anode target plate changes due to thermal expansion and contraction, the position of the focal point of the X-rays may be shifted, and the shift or offset of the focal point often causes artifacts in a reconstructed CT image. Therefore, it is desired to develop more accurate systems and methods for determining the offset of the position of the focal point of the X-ray tube.

SUMMARY

According to an aspect of the present disclosure, a method is provided. The method may be implemented on a computing device having at least one processor and at least one non-transitory storage medium. The method may include obtaining at least one parameter associated with an X-ray tube during a scan of a subject and obtaining a position of a focal point of the X-ray tube. The method may further include determining a target offset of the position of the focal point based on the at least one parameter and a target relationship between a plurality of reference parameters associated with the X-ray tube and a plurality of reference offsets of reference positions of the focal point. The method may further include causing, based on the target offset, a correction on the position of the focal point of the X-ray tube.

In some embodiments, the at least one parameter associated with the X-ray tube may include at least one of a thermal capacity of the X-ray tube, power of the X-ray tube, or a scanning duration.

In some embodiments, the target relationship may include at least one of: a first relationship between a plurality of reference thermal capacities and a plurality of reference offsets of reference positions of the focal point, or a second relationship among a plurality of predetermined values of reference power, a plurality of reference scanning durations, and a plurality of reference offsets of reference positions of the focal point.

In some embodiments, the second relationship may be determined by operations including: for each of the plurality of predetermined values of the reference power, obtaining a plurality of reference offsets of reference positions of the focal point corresponding to the plurality of reference scanning durations; and determining the second relationship based on the plurality of predetermined values of the reference power and the plurality of reference offsets of the reference positions of the focal point corresponding to the plurality of reference scanning durations.

In some embodiments, the determining a target offset of the position of the focal point may include determining a first offset of the position of the focal point based on the thermal capacity and the first relationship; determining a second offset of the position of the focal point based on the power, the scanning duration, the first offset, and the second relationship; and determining the target offset based on the first offset and the second offset.

In some embodiments, the determining the target offset based on the first offset and the second offset may include determining a difference between the first offset and the second offset, and determining the target offset based on the difference between the first offset and the second offset.

In some embodiments, the determining a second offset of the position of the focal point may include determining a first reference time based on the first offset, the power, and the second relationship; determining a second reference time based on the first reference time and the scanning duration; and determining the second offset based on the second reference time, the power, and the second relationship.

In some embodiments, the causing, based on the target offset, a correction on the position of the focal point of the X-ray tube may include causing electron beams in the X-ray tube to be adjusted by modifying, based on the target offset, at least one of an electric field or a magnetic field in the X-ray tube.

In some embodiments, the causing, based on the target offset, a correction on the position of the focal point of the X-ray tube may include obtaining scan data of the scan of the subject; generating corrected scan data based on the target offset; and reconstructing an image based on the corrected scan data.

In some embodiments, the target relationship between the plurality of reference parameters associated with the X-ray tube and the plurality of reference offsets of the reference positions of the focal point may be determined by operations including obtaining the plurality of reference parameters; obtaining the plurality of reference offsets of the reference positions of the focal point, wherein each of the plurality of reference offsets of the reference positions of the focal point corresponds to at least one of the plurality of reference parameters; and determining the target relationship by performing, on the plurality of reference parameters and the plurality of reference offsets, at least one of a mapping operation, a fitting operation, an interpolating operation, or a machine learning operation.

According to another aspect of the present disclosure, a system is provided. The system may include at least one non-transitory storage medium including a set of instructions and at least one processor in communication with the at least one non-transitory storage medium. When executing the set of instructions, the at least one processor may be configured to cause the system to perform operations including: obtaining at least one parameter associated with an X-ray tube during a scan of a subject; obtaining a position of a focal point of the X-ray tube; determining a target offset of the position of the focal point based on the at least one parameter and a target relationship between a plurality of reference parameters associated with the X-ray tube and a plurality of reference offsets of reference positions of the focal point; and causing, based on the target offset, a correction on the position of the focal point of the X-ray tube.

According to yet another aspect of the present disclosure, a non-transitory computer readable medium is provided. The non-transitory computer readable medium may include at least one set of instructions. When executed by at least one processor of a computing device, the at least one set of instructions may direct the at least one processor to perform operations including: obtaining at least one parameter associated with an X-ray tube during a scan of a subject; obtaining a position of a focal point of the X-ray tube; determining a target offset of the position of the focal point based on the at least one parameter and a target relationship between a plurality of reference parameters associated with the X-ray tube and a plurality of reference offsets of reference positions of the focal point; and causing, based on the target offset, a correction on the position of the focal point of the X-ray tube.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for focal point position correction according to some embodiments of the present disclosure;

FIG. 7 is a flowchart illustrating an exemplary process for establishing a target relationship between at least one parameter of the X-ray tube and a target offset of the position of the focal point according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
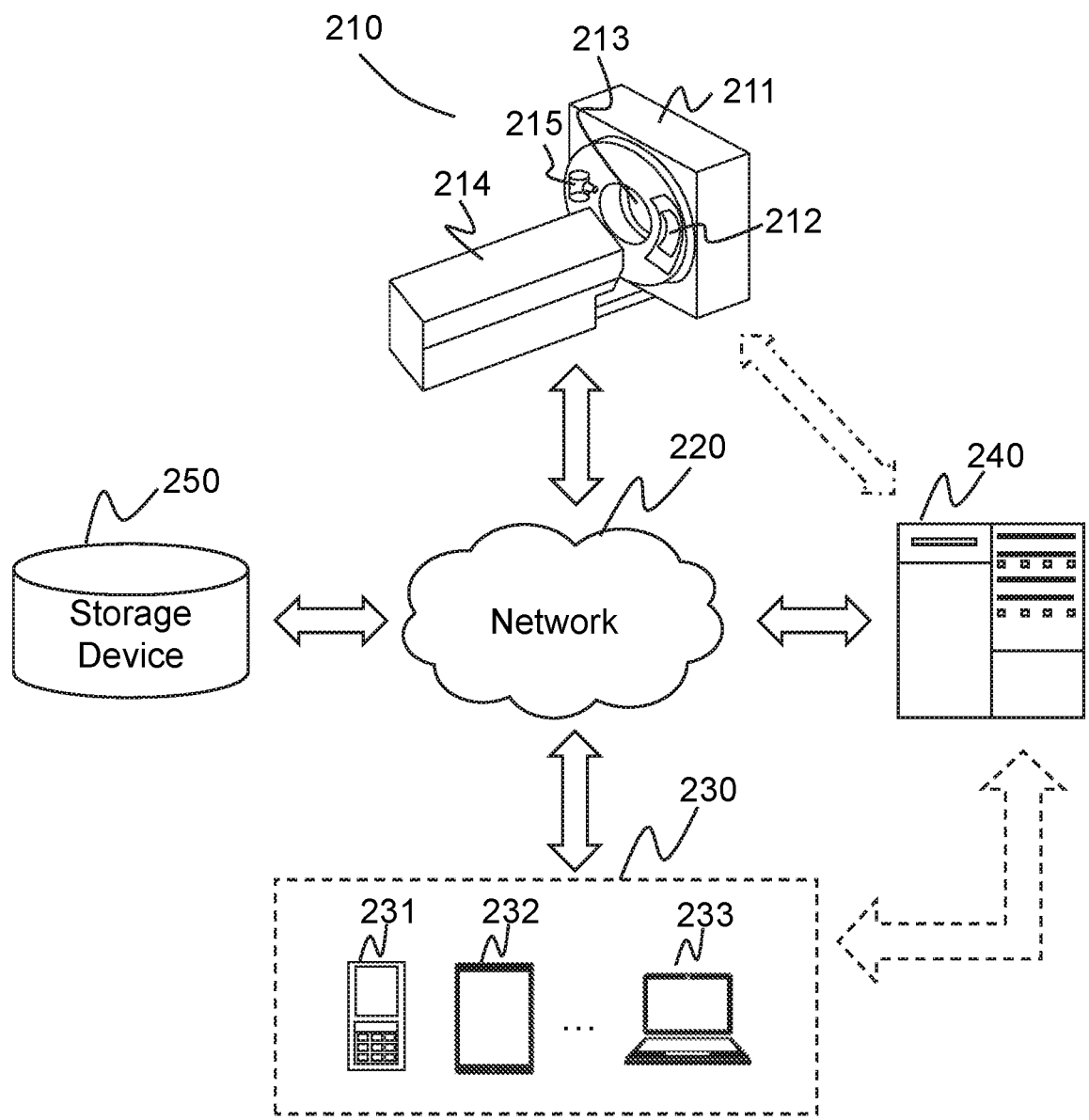
FIG. 2 is a schematic diagram illustrating an exemplary imaging system according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for an imaging system. In some embodiments, the imaging system may include a single modality imaging system and/or a multi-modality imaging system. The single modality imaging system may include, for example, an X-ray imaging system, an computed tomography (CT) system, a magnetic resonance imaging (MRI) system, an ultrasonography system, a positron emission tomography (PET) system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. It should be noted that the imaging system described below is merely provided for illustration purposes, and not intended to limit the scope of the present disclosure.

The present disclosure provides mechanisms (which can include methods, systems, computer-readable medium, etc.) for correcting the position of the focal point of an X-ray tube. For example, a target relationship between at least one parameter of the X-ray tube and the offset of the focal point of the X-ray tube may be determined. Parameters of the X-ray tube may include a thermal capacity of the X-ray tube, power of the X-ray tube, a scanning duration, or the like, or any combination thereof. At least one parameter of the X-ray tube during the scanning process may be obtained. The target offset of the position of the focal point may be determined based on the target relationship and the at least one parameter obtained during the scanning process. A correction may be performed on the position of the focal point based on the target offset.

FIG. 2 is a schematic diagram illustrating an exemplary imaging system_200 according to some embodiments of the present disclosure. As shown, the imaging system 200 may include an imaging device 210, a network 220, one or more terminals 230, a processing device 240, and a storage device 250. In some embodiments, the imaging device 210, the terminal(s) 230, the processing device 240, and/or the storage device 250 may be connected to and/or communicate with each other via a wireless connection (e.g., the network 220), a wired connection, or a combination thereof. The connection between the components of the imaging system 200 may be variable. Merely by way of example, the imaging device 210 may be connected to the processing device 240 through the network 220, as illustrated in FIG. 2. As another example, the imaging device 210 may be connected to the processing device 240 directly. As a further example, the storage device 250 may be connected to the processing device 240 through the network 220, as illustrated in FIG. 2, or connected to the processing device 240 directly. As still a further example, a terminal 230 may be connected to the processing device 240 through the network 220, as illustrated in FIG. 2, or connected to the processing device 240 directly.

The imaging device 210 may generate or provide image data via scanning a subject (e.g., a patient) disposed on a scanning table 214 of the imaging device 210. In some embodiments, the imaging device 210 may include a single-modality scanner and/or multi-modality scanner. The single-modality scanner may include, for example, a computed tomography (CT) scanner. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, or the like, or a combination thereof. In some embodiments, the image data may include scan data, images relating to the subject, etc. The scan data may be raw data generated by the imaging device 210 by scanning the subject. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or region of interest, such as an esophagus, a trachea, a bronchus, a stomach, a gallbladder, a small intestine, a colon, a bladder, a ureter, a uterus, a fallopian tube, etc. In some embodiments, the subject may be a phantom.

In some embodiments, the imaging device 210 may include a gantry 211, a detector 212, a detecting region 213, a scanning table 214, and a radioactive scanning source 215. The gantry 211 may support the detector 212 and the radioactive scanning source 215. A subject may be placed on the scanning table 214 to be scanned. The radioactive scanning source 215 may emit radioactive rays to the subject. The radiation may include a particle ray, a photon ray, or the like, or a combination thereof. In some embodiments, the radiation may include a plurality of radiation particles (e.g., neutrons, protons, electron, p-mesons, heavy ions), a plurality of radiation photons (e.g., X-ray, a y-ray, ultraviolet, laser), or the like, or a combination thereof. The detector 212 may detect radiations and/or radiation events (e.g., gamma photons) emitted from the detecting region 213. In some embodiments, the detector 212 may include a plurality of detector units. The detector units may include a scintillation detector (e.g., a cesium iodide detector) or a gas detector. The detector unit may be a single-row detector or a multi-rows detector.

In some embodiments, the imaging device 210 may be integrated with one or more other devices that may facilitate the scanning of the subject, such as an image-recording device. The image-recording device may be configured to take various types of images related to the subject. For example, the image-recording device may be a two-dimensional (2D) camera that takes pictures of the exterior or outline of the subject. As another example, the image-recording device may be a 3D scanner (e.g., a laser scanner, an infrared scanner, a 3D CMOS sensor) that records the spatial representation of the subject.

The network 220 may include any suitable network that can facilitate exchange of information and/or data for the imaging system 200. In some embodiments, one or more components of the imaging system 200 (e.g., the imaging device 210, the processing device 240, the storage device 250, the terminal(s) 230) may communicate information and/or data with one or more other components of the imaging system 200 via the network 220. For example, the processing device 240 may obtain image data from the imaging device 210 via the network 220. As another example, the processing device 240 may obtain user instruction(s) from the terminal(s) 230 via the network 220. The network 220 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 220 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 220 may include one or more network access points. For example, the network 220 may include wired and/or wireless network access points such as base stations and/or internet exchange points through which one or more components of the imaging system 200 may be connected to the network 220 to exchange data and/or information.

The terminal(s) 230 may be connected to and/or communicate with the imaging device 210, the processing device 240, and/or the storage device 250. For example, the terminal(s) 230 may obtain image data obtained via the imaging device 210 and transmit the image data to the processing device 240 to be processed. In some embodiments, the terminal(s) 230 may include a mobile device 231, a tablet computer 232, a laptop computer 233, or the like, or any combination thereof. For example, the mobile device 231 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 230 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 240 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 230 may be part of the processing device 240.

The processing device 240 may process data and/or information obtained from the imaging device 210, the storage device 250, the terminal(s) 230, or other components of the imaging system 200. For example, the processing device 240 may reconstruct an image based on scan data obtained by the imaging device 210. As another example, the processing device 240 may determine an offset of the position of the focal point of the radioactive scanning source 215. As yet another example, the processing device 240 may correct the scan data received from the imaging device 210 to compensate for the target offset. In some embodiments, the processing device 240 may be a single server or a server group. The server group may be centralized or distributed. In some embodiments, the processing device 240 may be local to or remote from the imaging system 200. For example, the processing device 240 may access information and/or data from the imaging device 210, the storage device 250, and/or the terminal(s) 230 via the network 220. As another example, the processing device 240 may be directly connected to the imaging device 210, the terminal(s) 230, and/or the storage device 250 to access information and/or data. In some embodiments, the processing device 240 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 240 may be implemented by a computing device 200 having one or more components as described in connection with FIG. 3.

The storage device 250 may store data, instructions, and/or any other information. In some embodiments, the storage device 250 may store data obtained from the processing device 240, the terminal(s) 230, and/or the storage device 250. In some embodiments, the storage device 250 may store data and/or instructions that the processing device 240 may execute or use to perform exemplary methods described in the present disclosure. In some embodiments, the storage device 250 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 250 may be implemented on a cloud platform as described elsewhere in the disclosure.

In some embodiments, the storage device 250 may be connected to the network 220 to communicate with one or more other components of the imaging system 200 (e.g., the processing device 240, the terminal(s) 230). One or more components of the imaging system 200 may access the data or instructions stored in the storage device 250 via the network 220. In some embodiments, the storage device 250 may be part of the processing device 240.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 250 may be a data storage including cloud computing platforms, such as public cloud, private cloud, community, and hybrid clouds, etc. However, those variations and modifications do not depart the scope of the present disclosure.

Figure 3:
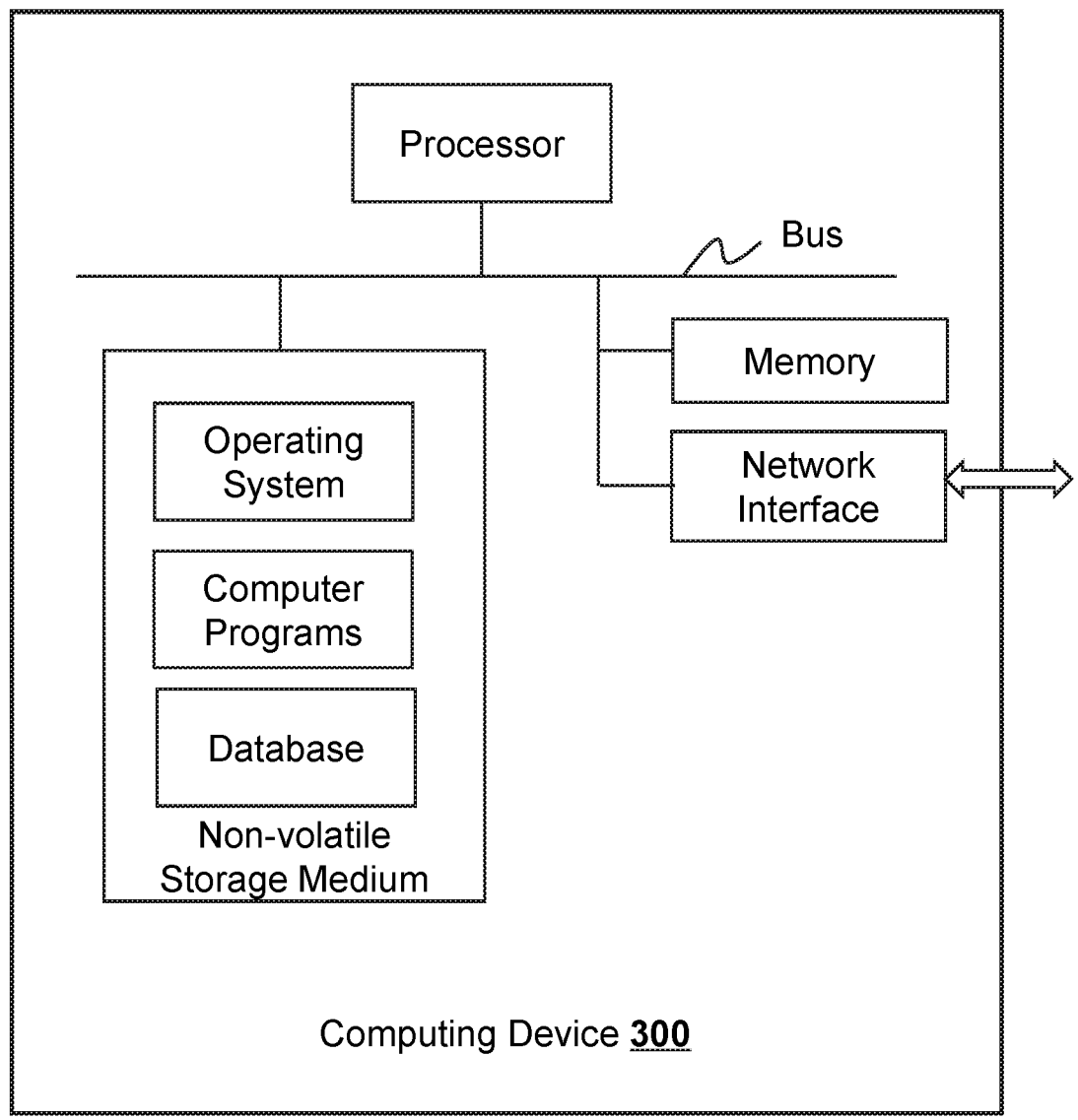
FIG. 3 is a schematic diagram illustrating exemplary hardware and/or software components of an exemplary computing device according to some embodiments of the present disclosure.

FIG. 3 is a schematic diagram illustrating exemplary hardware and/or software components of an exemplary computing device 300. In some embodiments, the processing device 240 may be implemented on the computing device 300. As illustrated in FIG. 3, the computing device 300 may include a processor and a storage connected through a bus. Computer programs may be stored in the storage (e.g., a non-volatile storage device). When the processor executes the computer programs, the processor may execute a method which will be described in connection with, for example, FIGS. 6-9. Optionally, the computing device may further include a network interface, a display, and an input device. The processor may be used to provide computing capabilities and generate controlling signals for controlling other components of the imaging system 200. The storage of the computing device may include a non-volatile storage medium and a memory. The non-volatile storage medium may store an operating system, computer programs, and a database. The memory may be used for executing the operating system and computer programs in the non-volatile storage medium. The network interface of the computing device may be used to communicate with an external terminal through a network connection.

The processor may execute computer instructions (e.g., program code) and perform functions of the processing device 240 in accordance with techniques described herein. The computer instructions may include, for example, routines, programs, objects, components, data structures, procedures, modules, and functions, which perform particular functions described herein. For example, the processor may process image data obtained from the imaging device 210, the terminals 230, the storage device 250, and/or any other component of the imaging system 200. In some embodiments, the processor may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, and thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operation s A and B).

The storage may store data/information obtained from the imaging device 210, the terminals 230, the storage device 250, and/or any other component of the imaging system 200. In some embodiments, the storage may include a mass storage device, a removable storage device, a volatile read-and-write memory, a read-only memory (ROM), or the like, or any combination thereof. For example, the mass storage may include a magnetic disk, an optical disk, solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage may store one or more programs and/or instructions to perform exemplary methods described in the present disclosure. For example, the storage may store a program for the processing device 240 for determining the position of a target region of a subject (e.g., a target portion of a patient).

The input device may be used to input signals, data, information, etc. In some embodiments, the input device may enable user interaction with the computing device 300. Examples of the input device may include a keyboard, a mouse, a touch screen, a microphone, or the like, or a combination thereof. Examples of the display may include a liquid crystal display (LCD), a light-emitting diode (LED)-based display, a flat panel display, a curved screen, a television device, a cathode ray tube (CRT), a touch screen, or the like, or a combination thereof.

The network interface may be connected to a network (e.g., the network 220) to facilitate data communications. For example, the network interface may establish connections between the processing device 240 and the imaging device 210, the terminals 230, and/or the storage device 250. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the network interface may be and/or include a standardized communication port, such as RS232, RS485, etc. In some embodiments, the network interface may be a specially designed communication port. For example, the network interface may be designed in accordance with the digital imaging and communications in medicine (DICOM) protocol.

It should be noted that the methods for focal point position correction provided in the present disclosure may be implemented on a focal point correction device. The focal point correction device may be implemented as part or all of the computing device 300 through software, hardware, or a combination thereof. In the following description, as an example for description, the methods are implemented on the computing device 300.

Figure 4:
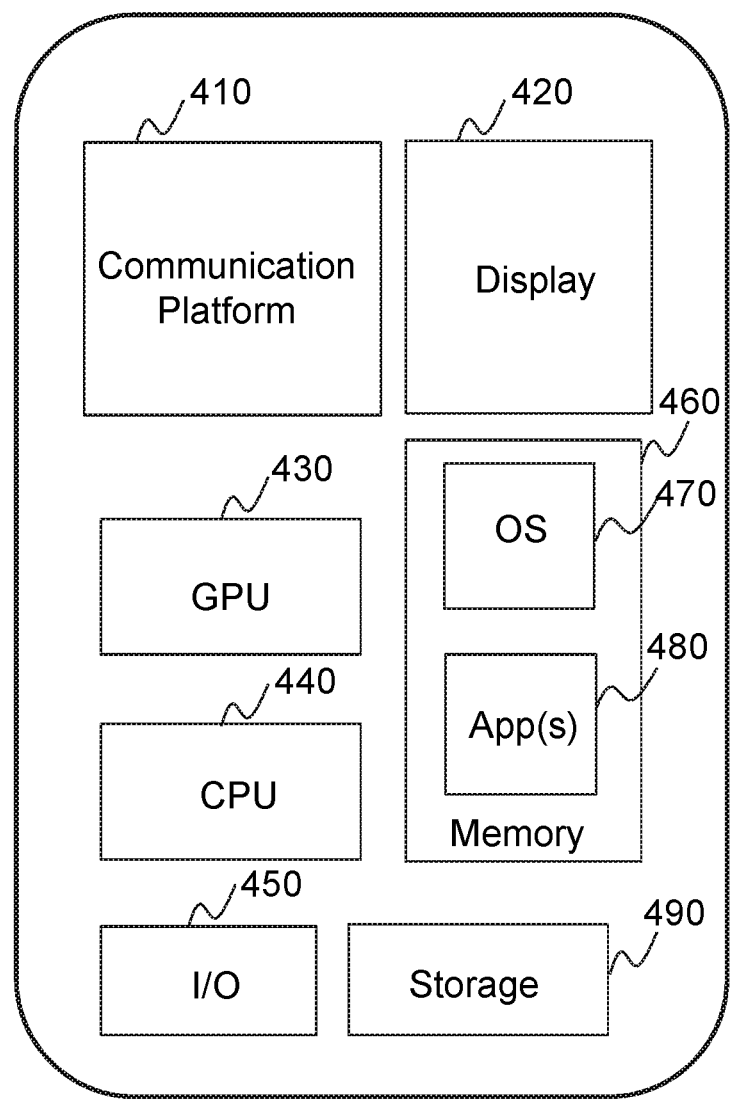
FIG. 4 is a schematic diagram illustrating exemplary hardware and/or software components of an exemplary mobile device according to some embodiments of the present disclosure.

FIG. 4 is a schematic diagram illustrating exemplary hardware and/or software components of an exemplary terminal device 400 according to some embodiments of the present disclosure. In some embodiments, the terminal 230 may be implemented as the terminal device 400. As illustrated in FIG. 4, the terminal device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the terminal device 400. In some embodiments, a mobile operating system 470 (e.g., iOS™' Android™, Windows Phone™) and one or more applications 480 may be loaded into the memory 460 from the storage 490 in order to be executed by the CPU 440. The applications 480 may include a browser or any other suitable mobile apps for receiving and rendering information relating to image processing or other information from the processing device 240. User interactions with the information stream may be achieved via the I/O 450 and provided to the processing device 240 and/or other components of the imaging system 200 via the network 220. For example, a user may view the target offset of the position of the focal point of the X-ray tube via the terminal device 400. As another example, the user may view an image reconstructed based on the scan data of the subject.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal. A computer may also act as a server if appropriately programmed.

Figure 5:
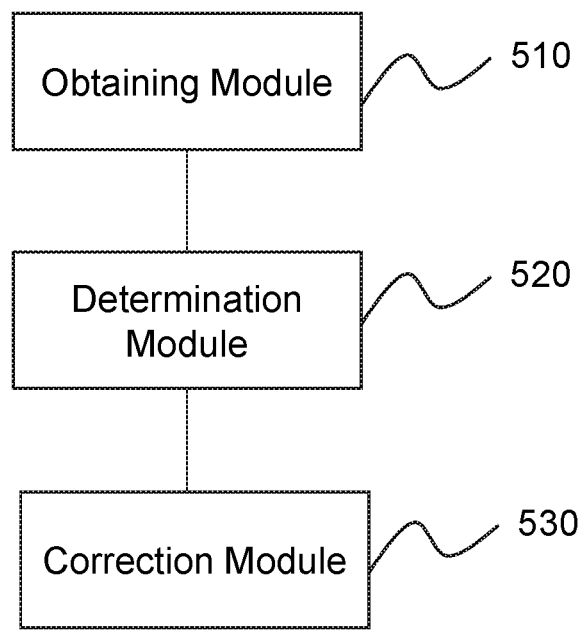
FIG. 5 is a block diagram illustrating an exemplary focal point correction device according to some embodiments of the present disclosure.

FIG. 5 is a block diagram illustrating an exemplary focal point correction device according to some embodiments of the present disclosure. As illustrated in FIG. 5, the focal point correction device may include an obtaining module 510, a determination module 520, and a correction module 530. In some embodiments, the modules may be hardware circuits of all or part of the processing device 240. The modules may also be implemented as an application or a set of instructions read and executed by the processing device 240. Further, the modules may be any combination of the hardware circuits and the application/instructions. For example, the modules may be a part of the processing device 240 when the processing device 240 is executing the application/set of instructions.

The obtaining module 510 may obtain at least one real-time parameter of the X-ray tube during the scanning process. In some embodiments, parameters (also referred to as working parameters) of the X-ray tube may include a thermal capacity of the X-ray tube, power of the X-ray tube, a scanning duration, or the like, or any combination thereof. In some embodiments, the obtaining module 510 may obtain the target relationship between the at least one parameter of the X-ray tube and the offset of the focal point of the X-ray tube, for example, from the storage device 250.

The determination module 520 may determine the target offset of the focal point according to the target relationship between the at least one parameter of the X-ray tube and the offset of the focal point of the X-ray tube. The target relationship between the at least one parameter and the offset of the focal point of the X-ray tube may include: a relationship between the thermal capacity of the X-ray tube and the offset of the focal point (also referred to as a first relationship); a relationship between the power of the X-ray tube and the offset of the focal point; a relationship between the scanning duration and the offset of the focal point. In some embodiments, the relationship between the power of the X-ray tube and the offset of the focal point and the relationship between the scanning duration and the offset of the focal point are jointly referred to as a second relationship.

In some embodiments, during the scanning process, the thermal capacity of the X-ray tube and the power of the X-ray tube may remain unchanged. As the scan of the subject continues, the change in the scanning duration may affect the offset of the focal point. In some embodiments, a first offset of the position of the focal point may be determined based on the thermal capacity of the X-ray tube and the first relationship, and a second offset of the position of the focal point may be determined based on the power, the scanning duration, the first offset, and the second relationship. A target offset of the position of the focal point may be determined based on the first offset and the second offset. For example, the target offset may be determined based on a difference between the first offset and the second offset.

The correction module 530 may cause a correction to be performed on the position of the focal point to be performed according to the target offset of the focal point. In some embodiments, the distribution of at least one of the electric field or magnetic field in the X-ray tube may be modified, so that the electron beams emitted by the X-ray tube is caused to shift accordingly to compensate for the target offset of the focal point caused by the at least one parameter of the X-ray tube. As a result, the electron beams emitted by the X-ray tube are still emitted to the desired focal point. In some embodiments, the correction on the position of the focal point may be performed by processing scan data during the scan of the subject. For example, a real-time target offset of the position of the focal point during the scanning process may be determined. Real-time scan data may be obtained and corrected based on the real-time target offset. An image (e.g., a two-dimensional image, a three-dimensional image) may be reconstructed based on the corrected real-time scan data.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the processing device 240 may include one or more additional modules. For example, the focal point correction device may further include a transmitting module configured to transmit data (such as the target offset) to other devices, such as the terminal 230.

FIG. 6 is a flowchart illustrating an exemplary process 600 for focal point position correction according to some embodiments of the present disclosure. At least a portion of process 600 may be implemented on the imaging system 200 as illustrated in FIG. 2 or the terminal device 400 as illustrated in FIG. 3. In some embodiments, one or more operations of the process 600 may be implemented in the imaging system 200 as illustrated in FIG. 2. In some embodiments, one or more operations in the process 600 may be stored in the storage device 260 as a form of instructions, and invoked and/or executed by the processing device 240. In some embodiments, the instructions may be transmitted in a form of electronic current or electrical signals.

In 602, at least one real-time parameter of the X-ray tube may be obtained during the scanning process. In some embodiments, operation 602 may be performed by the focal point correction device (e.g., the obtaining module 510).

Figure 1:
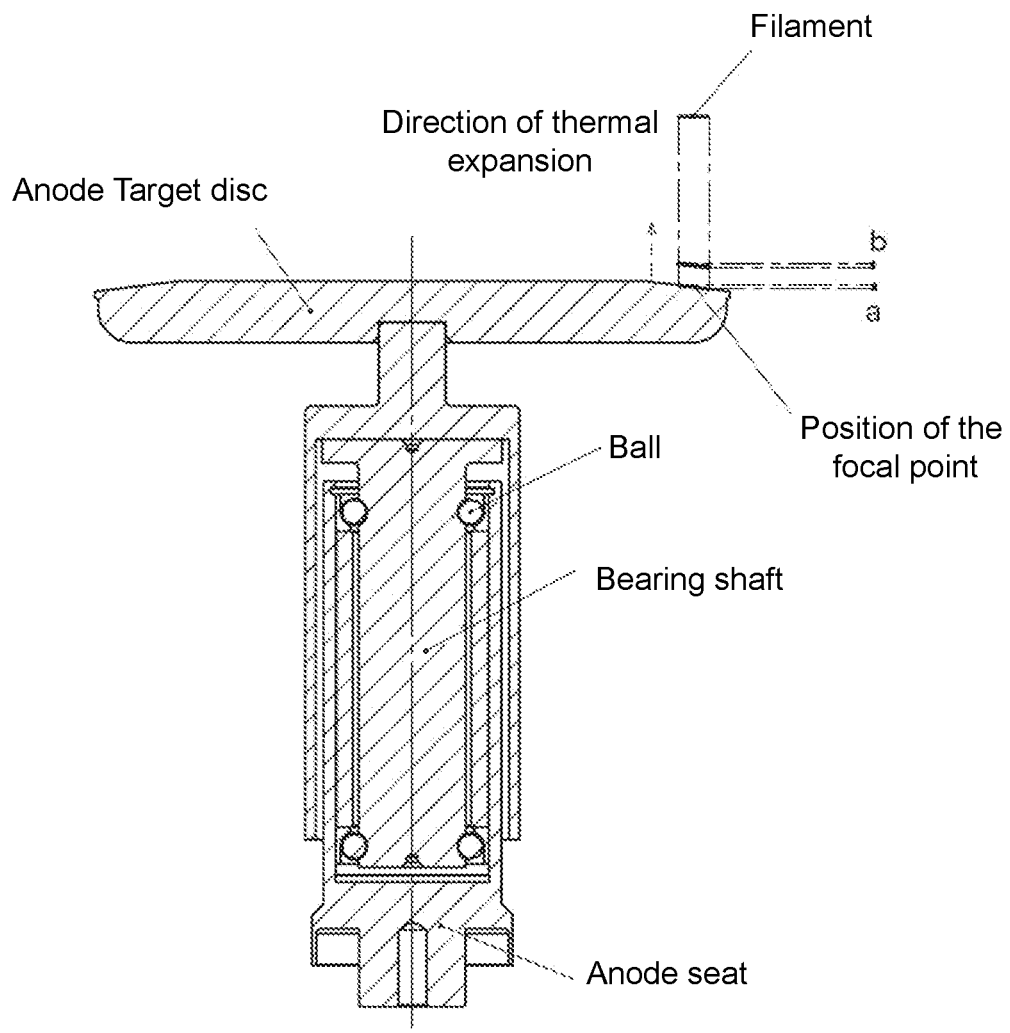
FIG. 1 is a schematic diagram illustrating a structure of an anode of an exemplary X-ray tube according to some embodiments of the present disclosure.

In some embodiments, parameters (also referred to as parameters) of the X-ray tube may include a thermal capacity of the X-ray tube, power of the X-ray tube, a scanning duration, or the like, or any combination thereof. For example, the thermal capacity may be presented as a percentage of the maximum thermal capacity of the X-ray tube. For example, the thermal capacity may be 40% of the maximum thermal capacity. During the scanning process, changes in at least one parameter of the X-ray tube may cause the position of the focal point of the X-ray tube to shift (i.e., to move to a different position). Specifically, in some existing CT systems, it takes some time (e.g., several minutes) for preheating the X-ray tube. A scan is started when the thermal capacity of the X-ray tube reaches a threshold. In some embodiments, the greater the thermal capacity of the X-ray tube is, the greater the offset of the focal point in the Z direction may be. As used herein, the term "Z direction" refers to a direction of thermal expansion of one or more components of the X-ray tube. FIG. 1 is a schematic diagram illustrating a structure of an anode of an exemplary X-ray tube according to some embodiments of the present disclosure. For example, as shown in FIG. 1, the Z direction may be parallel to the bearing shaft of the anode of the X-ray tube. It should be noted that the structure of the anode shown in FIG. 1 is illustrative, not intended to limit the scope of the present disclosure. The methods and systems for correcting the position of the focal point of the X-ray tube may be implemented on various structures of anodes.

In addition, there may be a correlation among the power of the X-ray tube, the scanning duration, and the offset of the position of the focal point of the X-ray tube. In some embodiments, during the scanning process, the thermal capacity and the power of the X-ray tube may remain unchanged, and the scanning duration may be obtained in real time during the scanning process.

In 604, the target offset of the focal point may be determined according to the target relationship between the at least one parameter of the X-ray tube and the offset of the focal point of the X-ray tube. In some embodiments, operation 604 may be performed by the focal point correction device (e.g., the determination module 520).

The target relationship between the at least one parameter and the offset of the focal point of the X-ray tube may include: a relationship between the thermal capacity of the X-ray tube and the offset of the focal point (also referred to as a first relationship); a relationship between the power of the X-ray tube and the offset of the focal point; a relationship between the scanning duration and the offset of the focal point. In some embodiments, the relationship between the power of the X-ray tube and the offset of the focal point and the relationship between the scanning duration and the offset of the focal point are jointly referred to as a second relationship. After the parameters of the X-ray tube are obtained, the offset of the focal point corresponding to different parameters may be determined according to the target relationship between the at least one parameter and the offset of the focal point of the X-ray tube.

In some embodiments, during the scanning process, the thermal capacity of the X-ray tube and the power of the X-ray tube may remain unchanged. As the scan of the subject continues, the change in the scanning duration may affect the offset of the focal point. In some embodiments, a first offset of the position of the focal point may be determined based on the thermal capacity of the X-ray tube and the first relationship, and a second offset of the position of the focal point may be determined based on the power, the scanning duration, the first offset, and the second relationship. The first offset refers to an offset of the position of the focal point generated during the preheating process. The second offset refers to an offset of the position of the focal point generated during the preheating process and the scanning process. The target offset of the position of the focal point may be determined based on the first offset and the second offset. As used herein, the target offset refers to an offset of the position of the focal point generated during the scanning process. For example, the target offset may be determined based on a difference between the first offset and the second offset.

In some embodiments, a plurality of reference parameters of the X-ray tube and a plurality of corresponding offsets of the focal point may be used as data for establishing an anode thermal analysis model of the X-ray tube. The target relationship between the at least one parameter and the offset of the focal point of the X-ray tube may be determined by the anode thermal analysis model based on the plurality of reference parameters of the X-ray tube and the plurality of corresponding offsets of the focal point. For example, the anode thermal analysis model may obtain the plurality of reference offsets of the reference positions of the focal point. Each of the plurality of reference offsets of the reference positions of the focal point corresponds to at least one of the plurality of reference parameters. The anode thermal analysis model may determine the target relationship by performing, on the plurality of reference parameters and the plurality of reference offsets, at least one of a mapping operation, a fitting operation, an interpolating operation, or a machine learning operation.

In some embodiments, to determine the second offset of the position of the focal point, the processing device 240 may be configured to determine a first reference time based on the first offset, the power, and the second relationship. The processing device 240 may be further configured to determine a second reference time based on the first reference time and the scanning duration. The second offset may be determined based on the second reference time, the power of the X-ray tube, and the second relationship. The process for determining the target offset will be described in more details through an example below.

Figure 8:
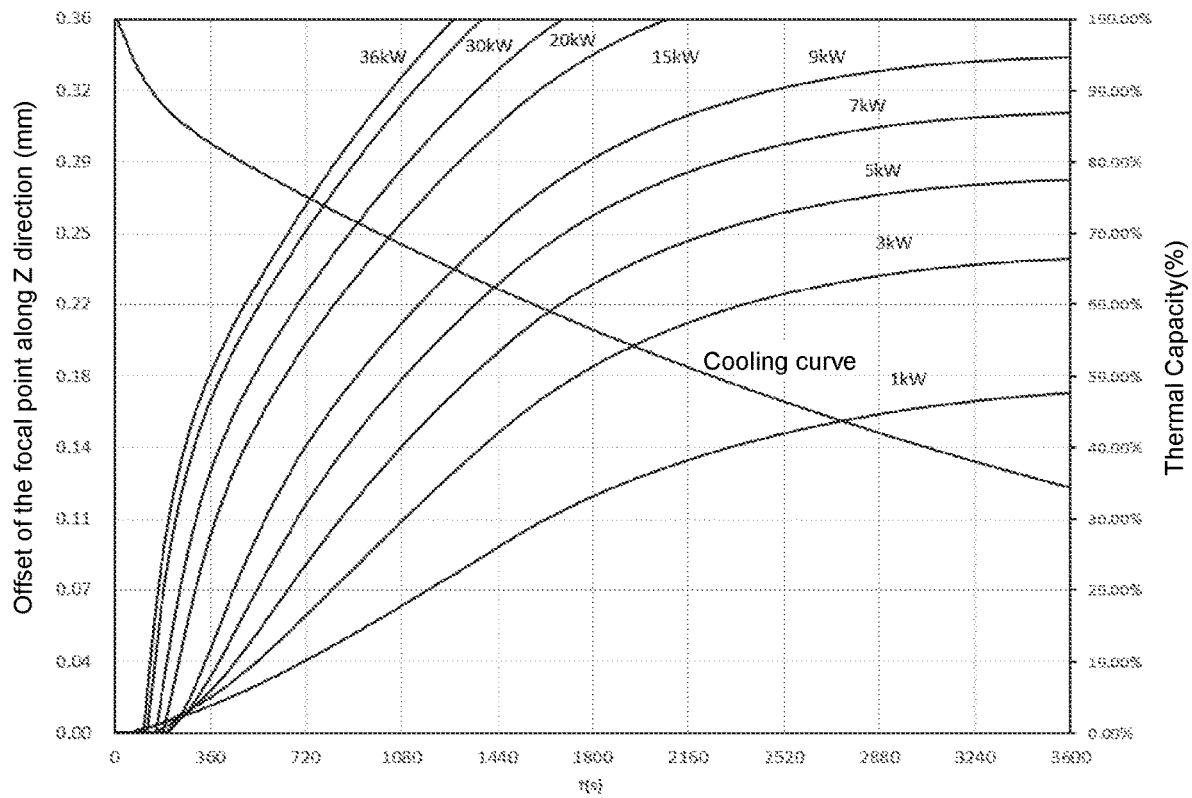
FIG. 8 is a schematic diagram illustrating an exemplary relationship between the at least one parameter of the X-ray tube and the target offset of the position of the focal point according to some embodiments of the present disclosure.

FIG. 8 is a schematic diagram illustrating an exemplary relationship between the at least one parameter of the X-ray tube and the target offset of the position of the focal point. As shown in FIG. 8, the horizontal axis represents the scanning duration, the left vertical axis represents the offset of the focal point along the Z direction, and the right vertical axis represents the thermal capacity of the X-ray tube. Firstly, assuming that the thermal capacity of the X-ray tube is 40%, according to the first relationship (e.g., illustrated by the cooling curve) between the thermal capacity and the offset of the focal point, it can be determined that the offset of the focal point in the Z direction (i.e., the first offset) is $X_1$. Secondly, it is assumed that the power of the X-ray tube for the scanning process is 7 kW, the scanning duration is 5 seconds (s), and if the offset of the position of the focal point in the Z direction is $X_1$, referring to the curve corresponding to 7 kW, the corresponding time is $t_1$ (i.e., the first reference time); then, based on the curve corresponding to 7 kW, the second offset of the focal point at $(t_1+5)$s (i.e., the second reference time) is $X_2$. Finally, the target offset of the focal point may be determined as $(X_2-X_1)$.

In 606, a correction on the position of the focal point may be caused to be performed according to the target offset of the focal point. In some embodiments, operation 606 may be performed by the focal point correction device (e.g., the correction module 530). After the target offset of the focal point is obtained, a correction on the position of the focal point may be performed to compensate for the target offset of the focal point.

In some embodiments, the distribution of at least one of the electric field or magnetic field in the X-ray tube may be dynamically modified, so that the electron beams emitted by the X-ray tube is caused to shift accordingly to compensate for the target offset of the focal point caused by the at least one parameter of the X-ray tube. As a result, the electron beams emitted by the X-ray tube are still emitted to the desired focal point.

For example, if the at least one parameter of the X-ray tube causes the position of the focal point to potentially shift by 0.216 mm in the Z direction, then the distribution of the electric field and/or the magnetic field of the X-ray tube is adjusted so that the emission direction of the electron beam is changed, so that the electron beam is still emitted to the desired position of the focal point.

In some embodiments, the position of the X-ray tube may be adjusted to compensate for the target offset of the focal point of the X-ray tube. For example, during the scanning process, the position of the X-ray tube may be dynamically adjusted based on the real-time target offset of the position of the focal point so that the actual position of the focal point is consistent with the original position of the focal point.

In some embodiments, the correction on the position of the focal point may be performed by processing scan data during the scan of the subject. For example, a real-time target offset of the position of the focal point during the scanning process may be determined. Real-time scan data may be obtained and corrected based on the real-time target offset. An image (e.g., a two-dimensional image, a three-dimensional image) may be reconstructed based on the corrected real-time scan data.

In the process of reconstructing an image such as a CT image, a geometric position of the focal point and the amount of movement of the focal point relative to the detector may need to be accurately obtained in order to rearrange the scan data. If the position of the focal point shifts, and the original position of the focal point is still used to reconstruct the image, artifacts may be caused in the reconstructed image. Taking the CT system as an example, the radioactive scanning source of the scanner in the CT system is the X-ray tube. X-rays are emitted from the X-ray tube to a region of interest of the subject. After the X-rays pass through the subject, at least a part of the X-rays may be received by the detector of the CT system as the scan data. The scan data may be used for image reconstruction. During the scanning process, the actual position of the focal point of the X-ray tube may change dynamically due to at least one parameter of the X-ray tube (such as the scanning duration), so the scan data received by the detector may need to be corrected accordingly. In some embodiments, the scan data obtained during the scanning process may be corrected to compensate for the influence of the target offset of the focal point on the scan data. For example, during image reconstruction, according to the target offset of the focal point, a preset algorithm is used to compensate and correct the scan data to compensate for the effect of the target offset of the focal point. Such a correction process may decrease artifacts in the reconstructed image.

The focal point position correction method provided in some embodiments (as described in connection to for example, FIG. 6) includes: obtaining real-time parameters of the X-ray tube during a scan; obtaining the target offset of the focal point according to the target relationship between the at least one parameter of the X-ray tube and the offset of the focal point of the X-ray tube; causing a correction on the position of the focal point to be performed. In some embodiments, the above focal point position correction method can compensate for the offset of the position of the focal point according to the target offset during the scanning process through software controlling, which does not have to involve a change in the hardware structure of the X-ray tube. Precise mechanical control, which is difficult to be realized for existing X-ray tube, can also be replaced by software controlling at a relatively low cost. As a result, the artifacts in the reconstructed image can be effectively decreased. The accuracy of the diagnosis analysis based on the reconstructed image can also be improved. In addition, the focal point correction method provided in this disclosure may be performed in a dynamic manner based on the real-time scan data and the real-time target offset of the position of the focal point of the X-ray tube. The quality of real-time images reconstructed based on the real-time scan data may be improved.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be omitted and/or one or more additional operations may be added. For example, the process 600 may further include an operation to send the reconstructed image to the storage device 250 and/or the terminal 230.

FIG. 7 is a flowchart illustrating an exemplary process 700 for establishing a target relationship between at least one parameter of the X-ray tube and a target offset of the position of the focal point according to some embodiments of the present disclosure. At least a portion of process 700 may be implemented on the imaging system 200 as illustrated in FIG. 2 or the terminal device 400 as illustrated in FIG. 4. In some embodiments, one or more operations of the process 700 may be implemented in the imaging system 200 as illustrated in FIG. 2. In some embodiments, one or more operations in the process 700 may be stored in the storage device 260 as a form of instructions, and invoked and/or executed by the processing device 240. In some embodiments, the instructions may be transmitted in a form of electronic current or electrical signals.

In 702, a first relationship between the thermal capacity of the X-ray tube and the offset of the focal point of the X-ray tube may be obtained.

In 704, reference offsets of the X-ray tube according to different reference power and reference scanning durations may be obtained to establish a second relationship among the power of the X-ray tube, the scanning duration, and the offset of the focal point of the X-ray tube.

In 706, a target relationship between the at least one parameter of the X-ray tube and the offset of the focal point may be determined based on the first relationship and the second relationship.

Before the correction on the position of the focal point is performed, a target relationship between the at least one parameter of the X-ray tube and the offset of the focal point needs to be established. In some embodiments, the target relationship may be stored in the storage device 250, for example, in the form of tables, curves, correlation functions, or the like, or any combination thereof. The influence of different parameters of the X-ray tube on the target offset of the focal point may be different, so the relationship between the thermal capacity of the X-ray tube and the offset of the focal point, the relationship between the power of the X-ray tube and the offset of the focal point, and the relationship between the scanning duration and the offset of the focal point need to be established separately. In some embodiments, the relationship between the power of the X-ray tube and the offset of the focal point and the relationship between the scanning duration and the offset of the focal point are jointly referred to as the second relationship among the power of the X-ray tube, the scanning duration, and the offset of the focal point of the X-ray tube.

Since the thermal capacity of the X-ray tube can remain the same during the scanning process, reference offsets of the focal point under different reference thermal capacities can be obtained to determine the first relationship. For example, according to the cooling curve shown in FIG. 6, which represents the first relationship, when the thermal capacity of the X-ray tube is 70%, the offset of the focal point may be 0.25 mm, and when the X-ray tube thermal capacity is 40%, the offset of the focal point may be 0.14 mm.

To establish the second relationship, the X-ray tube is controlled to emit X-rays to scan the subject at different powers under the same thermal capacity. For example, in difference reference scans, X-rays may be emitted at powers of 1 kW, 3 kW, 5 kW, 7 kW, 9 kW, or the like. In each of the reference scans, a subject (e.g., a phantom) is scanned for a preset time to obtain reference offsets of the focal point of the X-ray tube that change with reference scanning durations under the same power. For example, as shown in FIG. 8, the first relationship and the second relationship may be represented using the same coordinate system to represent the target relationship between the at least one parameter of the X-ray tube and the offset of the focal point.

It should be understood that although the operations in the flowcharts of FIGS. 6-7 can be sequentially performed according to the directions of the arrows, these operations may be performed in an order that is different from the order shown in FIGS. 6-7. Moreover, at least a part of the operations in FIG. 6 and FIG. 7 may include multiple sub-steps or multiple stages. These sub-steps or stages are not necessarily performed at the same time, but may be performed at different time.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "some embodiments," and "some embodiments" mean that a particular feature, structure or characteristic described in connection with the embodiment is included in at least one embodiment of the present disclosure. Therefore, it is emphasized and should be appreciated that two or more references to "some embodiments" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method implemented on a computing device having at least one processor and at least one non-transitory storage medium, the method comprising:
   obtaining at least one parameter associated with an X-ray tube during a scan of a subject;
   determining a target offset of a position of a focal point of the X-ray tube based on the at least one parameter and a target relationship between a plurality of reference parameters associated with the X-ray tube and a plurality of reference offsets of reference positions of the focal point of the X-ray tube; and
   causing, based on the target offset of the position of the focal point of the X-ray tube, a correction on the position of the focal point of the X-ray tube.

2. The method of claim 1, wherein the at least one parameter associated with the X-ray tube includes at least one of a thermal capacity of the X-ray tube, a power of the X-ray tube, or a scanning duration.

3. The method of claim 2, wherein the target relationship between the plurality of reference parameters associated with the X-ray tube and the plurality of reference offsets of reference positions of the focal point of the X-ray tube includes at least one of:
   a first relationship between a plurality of reference thermal capacities and the plurality of reference offsets of reference positions of the focal point of the X-ray tube, or
   a second relationship among a plurality of predetermined values of a reference power, a plurality of reference scanning durations, and the plurality of reference offsets of reference positions of the focal point of the X-ray tube.

4. The method of claim 3, further comprising:
   determining the second relationship by operations including:
   for each of the plurality of predetermined values of the reference power, obtaining the plurality of reference offsets of reference positions of the focal point of the X-ray tube corresponding to the plurality of reference scanning durations; and
   determining the second relationship based on the plurality of predetermined values of the reference power and the plurality of reference offsets of reference positions of the focal point of the X-ray tube corresponding to the plurality of reference scanning durations.

5. The method of claim 3, wherein the determining a target offset of the position of the focal point of the X-ray tube includes:
   determining a first offset of the position of the focal point of the X-ray tube based on the thermal capacity of the X-ray tube and the first relationship;
   determining a second offset of the position of the focal point of the X-ray tube based on the power of the X-ray tube, the scanning duration, the first offset, and the second relationship; and
   determining the target offset of the position of the focal point of the X-ray tube based on the first offset and the second offset.

6. The method of claim 5, wherein the determining the target offset of the position of the focal point of the X-ray tube based on the first offset and the second offset includes:
   determining a difference between the first offset and the second offset; and
   determining the target offset of the position of the focal point of the X-ray tube based on the difference between the first offset and the second offset.

7. The method of claim 5, wherein the determining a second offset of the position of the focal point of the X-ray tube includes:
   determining a first reference time based on the first offset of the position of the focal point of the X-ray tube, the power of the X-ray tube, and the second relationship;
   determining a second reference time based on the first reference time and the scanning duration; and
   determining the second offset of the position of the focal point of the X-ray tube based on the second reference time, the power of the X-ray tube, and the second relationship.

8. The method of claim 1, wherein the causing, based on the target offset of the position of the focal point of the X-ray tube, a correction on the position of the focal point of the X-ray tube includes:
   causing electron beams in the X-ray tube to be adjusted by modifying, based on the target offset of the position of the focal point of the X-ray tube, at least one of an electric field or a magnetic field in the X-ray tube.

9. The method of claim 1, wherein the causing, based on the target offset of the position of the focal point of the X-ray tube, a correction on the position of the focal point of the X-ray tube includes:
   obtaining scan data of the scan of the subject;
   generating corrected scan data based on the target offset of the position of the focal point of the X-ray tube; and
   reconstructing an image based on the corrected scan data.

10. The method of claim 1, wherein the target relationship between the plurality of reference parameters associated with the X-ray tube and the plurality of reference offsets of reference positions of the focal point of the X-ray tube is determined by operations including:
    obtaining the plurality of reference parameters;
    obtaining the plurality of reference offsets of reference positions of the focal point of the X-ray tube, wherein each of the plurality of reference offsets of reference positions of the focal point of the X-ray tube corresponds to at least one of the plurality of reference parameters; and determining the target relationship by performing, on the plurality of reference parameters and the plurality of reference offsets, at least one of a mapping operation, a fitting operation, an interpolating operation, or a machine-learning operation.

11. A system, comprising:

at least one non-transitory storage medium including a set of instructions; and at least one processor in a communication with the at least one non-transitory storage medium, wherein when executing the set of instructions, the at least one processor is configured to perform operations including:

obtaining at least one parameter associated with an X-ray tube during a scan of a subject;

determining a target offset of a position of a focal point of the X-ray tube based on the at least one parameter and a target relationship between a plurality of reference parameters associated with the X-ray tube and a plurality of reference offsets of reference positions of the focal point of the X-ray tube; and causing, based on the target offset of the position of the focal point of the X-ray tube, a correction on the position of the focal point of the X-ray tube.

12. The system of claim 11, wherein the at least one parameter associated with the X-ray tube includes at least one of a thermal capacity of the X-ray tube, a power of the X-ray tube, or a scanning duration.

13. The system of claim 12, wherein the target relationship between the plurality of reference parameters associated with the X-ray tube and the plurality of reference offsets of reference positions of the focal point of the X-ray tube includes at least one of:

a first relationship between a plurality of reference thermal capacities and the plurality of reference offsets of reference positions of the focal point of the X-ray tube, or a second relationship among a plurality of predetermined values of a reference power, a plurality of reference scanning durations, and the plurality of reference offsets of reference positions of the focal point of the X-ray tube.

14. The system of claim 13, wherein the at least one processor is further configured to determine the second relationship by operations including:

for each of the plurality of predetermined values the reference power, obtaining the plurality of reference offsets of reference positions of the focal point of the X-ray tube corresponding to the plurality of reference scanning durations; and determining the second relationship based on the plurality of predetermined values of the reference power and the plurality of reference offsets of reference positions of the focal point of the X-ray tube corresponding to the plurality of reference scanning durations.

15. The system of claim 13, wherein to determine the target offset of the position of the focal point of the X-ray tube, the at least one processor is further configured to perform operations including:

determining a first offset of the position of the focal point of the X-ray tube based on the thermal capacity of the X-ray tube and the first relationship;

determining a second offset of the position of the focal point of the X-ray tube based on the power of the X-ray tube, the scanning duration, the first offset, and the second relationship; and determining the target offset of the position of the focal point of the X-ray tube based on the first offset and the second offset.

16. The system of claim 15, wherein to determine the target offset of the position of the focal point of the X-ray tube based on the first offset and the second offset, the at least one processor is configured to perform operations including:

determining a difference between the first offset and the second offset; and determining the target offset of the position of the focal point of the X-ray tube based on the difference between the first offset and the second offset.

17. The system of claim 15, wherein to determine the second offset of the position of the focal point of the X-ray tube, the at least one processor is further configured to perform operations including:

determining a first reference time based on the first offset of the position of the focal point of the X-ray tube, the power of the X-ray tube, and the second relationship;

determining a second reference time based on the first reference time and the scanning duration; and determining the second offset of the position of the focal point of the X-ray tube based on the second reference time, the power of the X-ray tube, and the second relationship.

18. The system of claim 11, wherein the at least one processor is further configured to perform operations including:

causing electron beams in the X-ray tube to be adjusted by modifying, based on the target offset of the position of the focal point of the X-ray tube, at least one of an electric field or a magnetic field in the X-ray tube.

19. The system of claim 11, wherein the at least one processor is further configured to perform operations including:

obtaining scan data of the scan of the subject;

generating corrected scan data based on the target offset of the position of the focal point of the X-ray tube; and reconstructing an image based on the corrected scan data.

20. A non-transitory_computer-readable medium, comprising at least one set of instructions, wherein when executed by at least one processor of a computing device, the at least one set of instructions direct the at least one processor to perform operations including:

obtaining at least one parameter associated with an X-ray tube during a scan of a subject;

determining a target offset of a position of a focal point of the X-ray tube based on the at least one parameter and a target relationship between a plurality of reference parameters associated with the X-ray tube and a plurality of reference offsets of reference positions of the focal point of the X-ray tube; and causing, based on the target offset of the position of the focal point of the X-ray tube, a correction on the position of the focal point of the X-ray tube.

* * * * *